(12) United States Patent
Holmes

(10) Patent No.: US 8,287,742 B2
(45) Date of Patent: Oct. 16, 2012

(54) METHOD FOR SEPARATING A COMPOSITE LIQUID INTO AT LEAST TWO COMPONENTS

(75) Inventor: Brian M. Holmes, Evergreen, CO (US)

(73) Assignee: Terumo BCT, Inc., Lakewood, CO (US)

( * ) Notice: Subject to any disclaimer, the term of this patent is extended or adjusted under 35 U.S.C. 154(b) by 810 days.

(21) Appl. No.: 11/950,640

(22) Filed: Dec. 5, 2007

(65) Prior Publication Data

US 2008/0149564 A1 Jun. 26, 2008

Related U.S. Application Data

(60) Provisional application No. 60/870,860, filed on Dec. 20, 2006.

(51) Int. Cl.
*B01D 33/15* (2006.01)
*B01D 21/26* (2006.01)
*B01D 37/00* (2006.01)

(52) U.S. Cl. ........ 210/782; 210/147; 210/651; 210/749; 210/787; 210/790

(58) Field of Classification Search .............. 210/651, 210/749, 147, 787
See application file for complete search history.

(56) References Cited

U.S. PATENT DOCUMENTS

| 3,297,244 A | 1/1967 | Hein |
| 3,326,458 A | 6/1967 | Meryman et al. |
| 3,679,128 A * | 7/1972 | Unger et al. ............ 494/85 |
| 3,708,110 A | 1/1973 | Unger et al. |
| 3,724,747 A | 4/1973 | Unger et al. |
| 3,737,096 A | 6/1973 | Jones et al. |
| 3,858,796 A | 1/1975 | Unger et al. |
| 3,987,961 A | 10/1976 | Sinn et al. |
| 4,146,172 A | 3/1979 | Cullis et al. |
| 4,389,207 A | 6/1983 | Bacehowski et al. |
| 4,405,079 A | 9/1983 | Schoendorfer |
| 4,421,503 A | 12/1983 | Latham, Jr. et al. |

(Continued)

FOREIGN PATENT DOCUMENTS

EP 0097455 1/1984

(Continued)

OTHER PUBLICATIONS

International Search Report for PCT/US2007/086454, mailed May 19, 2008.

*Primary Examiner* — Krishnan S Menon
*Assistant Examiner* — Dirk Bass
(74) *Attorney, Agent, or Firm* — John R. Merkling

(57) ABSTRACT

Method for separating a volume of whole blood into at least a plasma component and a red blood cell component comprising centrifuging a separation bag containing a volume of whole blood so as to separate therein at least a first component comprising plasma and a second component comprising red blood cells; transferring the first component into a plasma component bag during centrifugation of the separation bag; transferring into the separation bag a volume of wash solution from a wash solution bag during centrifugation of the separation bag; mixing the volume of wash solution with the second component; centrifuging the separation bag so as to separate therein a washed red blood cell component and a supernatant component; and transferring the supernatant component into a waste bag during centrifugation of the separation bag.

20 Claims, 9 Drawing Sheets

U.S. PATENT DOCUMENTS

| | | | |
|---|---|---|---|
| 4,482,342 A | | 11/1984 | Lueptow et al. |
| 4,668,214 A | * | 5/1987 | Reeder ............................. 494/37 |
| 4,720,284 A | | 1/1988 | McCarty |
| 4,850,995 A | | 7/1989 | Tie et al. |
| 4,990,132 A | | 2/1991 | Unger et al. |
| 5,114,396 A | | 5/1992 | Unger et al. |
| 5,141,486 A | | 8/1992 | Antwiler |
| 5,427,695 A | | 6/1995 | Brown |
| 5,478,479 A | * | 12/1995 | Herrig ........................... 210/787 |
| 5,543,062 A | | 8/1996 | Nishimura |
| 5,632,906 A | | 5/1997 | Ishida et al. |
| 5,637,082 A | | 6/1997 | Pages et al. |
| 5,651,766 A | * | 7/1997 | Kingsley et al. ............. 604/6.04 |
| 5,723,050 A | | 3/1998 | Unger et al. |
| 5,738,644 A | | 4/1998 | Holmes et al. |
| 5,874,208 A | | 2/1999 | Unger |
| 5,904,355 A | | 5/1999 | Powers |
| 5,964,724 A | | 10/1999 | Rivera et al. |
| 6,039,711 A | | 3/2000 | Headley et al. |
| 6,261,217 B1 | | 7/2001 | Unger et al. |
| 6,296,602 B1 | | 10/2001 | Headley |
| 6,315,706 B1 | | 11/2001 | Unger et al. |
| 6,348,031 B1 | | 2/2002 | Unger et al. |
| 6,439,577 B2 | | 8/2002 | Jorgensen et al. |
| 6,656,105 B2 | | 12/2003 | Hogberg et al. |
| 6,855,102 B2 | * | 2/2005 | Unger et al. ...................... 494/37 |
| 2002/0119880 A1 | | 8/2002 | Hogberg et al. |
| 2004/0026341 A1 | | 2/2004 | Hogberg et al. |
| 2004/0104182 A1 | * | 6/2004 | Holmes et al. ................ 210/787 |
| 2005/0045567 A1 | * | 3/2005 | Holmes et al. ................ 210/782 |
| 2006/0205581 A1 | * | 9/2006 | Chammas ........................ 494/16 |
| 2007/0179423 A1 | | 8/2007 | Felt et al. ...................... 604/6.01 |
| 2007/0284320 A1 | * | 12/2007 | Menhennett et al. .......... 210/782 |
| 2008/0053203 A1 | | 3/2008 | Hogberg et al. .............. 73/61.44 |
| 2008/0093312 A1 | * | 4/2008 | Holmes et al. ................ 210/787 |
| 2008/0283473 A1 | * | 11/2008 | Holmes et al. ................ 210/787 |

FOREIGN PATENT DOCUMENTS

| | | |
|---|---|---|
| EP | 0499891 | 8/1992 |
| EP | 0682953 | 11/1995 |
| EP | 0771569 | 5/1997 |
| EP | 1709983 | 11/2005 |
| WO | WO 92/00145 | 1/1992 |
| WO | WO96/40319 | 12/1996 |
| WO | WO 01/02037 | 1/2001 |
| WO | WO 01/97943 | 12/2001 |
| WO | WO 03/089027 | 10/2003 |
| WO | WO 2004/018021 | 3/2004 |
| WO | WO2006/071496 | 7/2006 |

* cited by examiner

US 8,287,742 B2

METHOD FOR SEPARATING A COMPOSITE LIQUID INTO AT LEAST TWO COMPONENTS

CROSS REFERENCE TO RELATED APPLICATIONS

This application claims the benefit of U.S. Provisional Application No. 60/870,860 filed Dec. 20, 2006.

FIELD OF THE INVENTION

The present invention concerns an apparatus and a method for separating a volume of composite liquid into at least two components.

BACKGROUND

The apparatus and method of the invention are particularly appropriate for the separation of biological fluids comprising an aqueous component and one or more cellular components. For example, potential uses of the invention include extracting, from a volume of whole blood, a plasma component and a red blood cell component, or a platelet rich plasma component and a red blood cell component, or a plasma component, a platelet/mononuclear cell component, and a red blood cell component.

European patent application EP 1 709 983 describes a method and an apparatus for separating a volume of whole blood into at least three components in accordance with various separation protocols. For example, one protocol provides for the separation of a volume of whole blood into a plasma component, a red blood cell component, and mononuclear cell component (including a volume of plasma, platelets, mononuclear cells and residual red blood cells). The apparatus comprises a centrifuge adapted to cooperate with various bag sets, including a bag set comprising an annular separation bag, which is connected to three satellites bags, including a bag for plasma, a bag for a mononuclear cell component, and a bag for a red blood cell component bag. The centrifuge includes a rotor for spinning the separation bag and centrifuging the whole blood contained therein, the rotor having a turntable for supporting the separation bag and a central compartment for containing the component bags connected to the separation bag; and a squeezing system for squeezing the separation bag and causing the transfer of at least a plasma component into the plasma component bag and a mononuclear cell component into the mononuclear cell component bag.

According to European patent application EP 1 709 983, a method for separating a volume of whole blood contained in a separation bag into at least three components comprises the steps of centrifuging the separation bag so as to separate therein a first inner layer comprising plasma, a second intermediate layer comprising platelets, a third intermediate layer comprising lymphocytes, monocytes and granulocytes and a fourth outer layer comprising red blood cells, wherein at least the third and fourth layers partially overlap; transferring, into a plasma component bag connected to the separation bag, a plasma component substantially comprising a first fraction of the first layer; and transferring, into a mononuclear cell component bag connected to the separation bag, a mononuclear cell component comprising at least a fraction of the third layer comprising lymphocytes and monocytes.

This method allows for the separation of a red blood cell component substantially devoid of mononuclear cells, which for various reasons are undesirable in transfusible red blood cells.

White blood cells are not the only contaminant that it is desirable to remove at least partially from a red blood cell component in which red blood cells are packed into a residual volume of plasma that may contain undesirable proteins (e.g. prions) and viruses.

SUMMARY OF THE INVENTION

One object of the invention is to design a method and an apparatus for the separation whole blood allowing for the preparation of a transfusible red blood cell product from which plasma has been removed.

According to the invention, a method for separating a volume of whole blood into at least a plasma component and a red blood cell component comprises centrifuging a separation bag containing a volume of whole blood so as to separate therein at least a first component comprising plasma and a second component comprising red blood cells; transferring the first component into a plasma component bag connected to the separation bag, during centrifugation of the separation bag; transferring into the separation bag a volume of wash solution from a wash solution bag connected to the separation bag, during centrifugation of the separation bag; mixing the volume of wash solution with the second component; centrifuging the separation bag so as to separate therein a washed red blood cell component and a supernatant component comprising used wash solution; and transferring the supernatant component into a waste bag connected to the separation bag, during centrifugation of the separation bag.

The method may further comprise transferring the volume of whole blood into the separation bag from a whole blood bag connected to the separation bag. Also the volume of whole blood maybe transferred by centrifugation from the whole blood bag into the separation bag. The separation bag is centrifuged so as to separate therein a first component comprising plasma, a second component comprising red blood cells, and an intermediate component comprising platelets and mononuclear cells.

The method further comprises transferring the intermediate component into an intermediate component bag connected to the separation bag during centrifugation of the separation bag.

The method may further comprise transferring the volume of whole blood into the separation bag from a whole blood bag connected to the separation bag; and transferring the intermediate component into the whole blood bag, after the volume of whole blood has been transferred into the separation bag.

The volume of wash solution is transferred by centrifugation into the separation bag. The volume of wash solution that is transferred into the separation bag substantially corresponds to a total volume of wash solution initially contained in the wash solution bag.

The supernatant component is transferred into the wash solution bag, which is used as a waste bag after the wash solution has been transferred into the separation bag. The volume of wash solution that is transferred into the separation bag is a first fraction of a total volume of wash solution initially contained in the wash solution bag. The method further comprises transferring the volume of whole blood into the separation bag from a whole blood bag connected to the separation bag; and transferring the supernatant component from the separation bag into the whole blood bag, which is used as a waste bag after the volume of whole blood has been transferred into the separation bag.

The method further comprises, after transferring the supernatant component into a waste bag: transferring into the separation bag a second fraction of the total volume of wash solution initially contained in the wash solution bag, during centrifugation of the separation bag; mixing the wash solution with the second component; centrifuging the separation bag so as to separate therein a washed red blood cell component and a supernatant component comprising used wash solution; and transferring the supernatant component into the waste bag during centrifugation of the separation bag.

Mixing the volume of wash solution with the second component comprises varying the centrifugation speed. Also mixing the volume of wash solution with the second component may comprise subjecting the separation bag to back and forth movement around a rotation axis.

The method further comprises initially enclosing the separation bag in a separation compartment having a fixed internal volume.

Transferring the first component into a plasma component bag comprises allowing a fluid communication between the separation bag and the plasma component bag; and pumping a fluid into the separation compartment so as to squeeze the separation bag until the first component has substantially been transferred into the plasma component bag.

Transferring a volume of wash solution into the separation bag comprises: pumping a volume of fluid from the separation compartment after the first component has been transferred into the plasma component bag; and allowing a fluid communication between the separation bag and the wash solution bag so as to transfer a volume of wash solution into the separation bag. The volume of fluid that is pumped out of the separation compartment substantially corresponds to a determined volume of wash solution to be transferred into the separation bag.

The method further comprises transferring a volume of storage solution for red blood cells into the separation bag, after transferring the supernatant component into the waste bag. The volume of storage solution is initially contained in a red blood cell product bag connected to the separation bag and the volume of storage solution is transferred from the red blood cell product bag into the separation bag.

The method further comprises mixing the volume of storage solution with the second component.

The method further comprises transferring the mixture of storage solution and second component into the red blood cell product bag.

The method further comprises filtering the mixture of storage solution and second component through a leuko-depletion filter while the mixture is being transferred into the red blood cell product bag.

According to the invention, an apparatus for separating a volume of whole blood contained in a separation bag into at least a plasma component and a red blood cell component, the separation bag being fluidly connected to at least three satellite bags, comprises a rotor for spinning the separation bag around a rotation axis of the rotor comprising: a separation compartment for containing the separation bag; and a container for containing the at least three satellite bags so that the satellite bags are closer to the rotation axis than a separation bag within the separation compartment; a first valve member mounted on the rotor for interacting with a tube connecting the separation bag to a first satellite bag and selectively allowing or blocking a fluid flow therethrough, wherein the first satellite bag is for initially containing a volume of whole blood; a second valve member mounted on the rotor for interacting with a tube connecting the separation bag to a second satellite bag and selectively allowing or blocking a fluid flow component therethrough, wherein the second satellite bag is for initially containing a volume of wash solution; a third valve member mounted on the rotor for interacting with a tube connecting the separation bag to a third satellite bag and selectively allowing or blocking a fluid flow component therethrough, wherein the third satellite bag is for ultimately containing a plasma component; a pumping system for pumping a fluid into the separation compartment and causing a transfer of a content of the separation bag into at least two of the three satellite bags; and a control unit programmed for: causing the rotor to rotate at a centrifugation speed allowing for the sedimentation of a volume of whole blood contained in a separation bag into at least an inner layer comprising plasma, and an outer layer comprising red blood cells; causing the third valve member to open the tube connected to the third satellite bag, wherein the first and second valve members are closed; causing the pumping system to pump fluid into the separation compartment and transfer into the third satellite bag a plasma component comprising a major fraction of the inner layer; causing the third valve member to close the tube connected to the third satellite bag; causing the pumping system to pump a volume of fluid from the separation compartment; causing the second valve member to open the tube connected to the second satellite bag, whereby a volume of wash solution is transferred by centrifugation from the second satellite bag into the separation bag; causing the rotor to mix the volume of wash solution with the outer layer and a remaining fraction of the inner layer; causing the rotor to rotate at a centrifugation speed allowing for the sedimentation of an inner layer comprising a supernatant, and an outer layer comprising washed red blood cells; causing one of the first and second valves to open a tube connecting the separation bag to the first or the second satellite bags, respectively; and causing the pumping system to pump fluid into the separation compartment and transfer the supernatant into the first or the second satellite bags.

The control unit may be further programmed for: causing the pumping system to pump a volume of fluid from the separation compartment corresponding to at least a total volume of wash solution contained in the second satellite bag; causing the second valve member to open the tube connected to the second satellite bag, whereby the total volume of wash solution is transferred by centrifugation from the second satellite bag into the separation bag; causing the second valve to open the tube connecting the separation bag to the second satellite bag, after sedimentation of an inner layer comprising a supernatant and an outer layer comprising washed red blood cells; and causing the pumping system to pump fluid into the separation compartment and transfer the supernatant into the second satellite bag.

The control unit also may be further programmed for causing the pumping system to pump a volume of fluid from the separation compartment corresponding to a determined fraction of a total volume of wash solution contained in the second satellite bag; causing the second valve member to open the tube connected to the second satellite bag, whereby the determined fraction of the total volume of wash solution is transferred by centrifugation from the second satellite bag into the separation bag; causing the first valve to open the tube connecting the separation bag to the first satellite bag, after sedimentation of an inner layer comprising a supernatant and an outer layer comprising washed red blood cells; and causing the pumping system to pump fluid into the separation compartment and transfer the supernatant into the first satellite bag.

The control unit may further be programmed for causing the rotor to rotate at a centrifugation speed allowing for the sedimentation of a volume of whole blood into at least a first inner layer comprising plasma, a second outer layer comprising red blood cells, and an intermediate layer comprising platelets and mononuclear cells; causing the first valve member to open the tube connecting the separation bag to the first satellite bag, wherein the second and third valve members are closed, when the plasma component has been transferred into the third satellite bag; and causing the pumping system to pump fluid into the separation compartment and transfer into the first satellite bag an intermediate component comprising platelets and mononuclear cells.

The control unit may further be programmed for initially causing the first valve member to open the tube connecting the separation bag to the first satellite bag, wherein the second and third valve members are closed and the first satellite bag contains a volume of whole blood; and causing the rotor to rotate at a centrifugation speed allowing for a transfer by centrifugation of the volume of whole blood from the first satellite bag into the separation bag.

The control unit may further be programmed for causing the rotor to mix the volume of wash solution with the outer layer and a remaining fraction of the inner layer by varying a rotation speed of the rotor between a higher rotation speed and a lower rotation speed.

The control unit may further be programmed for causing the rotor to mix the volume of wash solution with the outer layer and a remaining fraction of the inner layer by stopping the rotor and causing the rotor to rotate alternately in one direction and in the opposite direction around the rotation axis.

Other features and advantages of the invention will appear from the following description and accompanying drawings, which are to be considered exemplary only.

DESCRIPTION OF THE EMBODIMENTS

Figure 1:
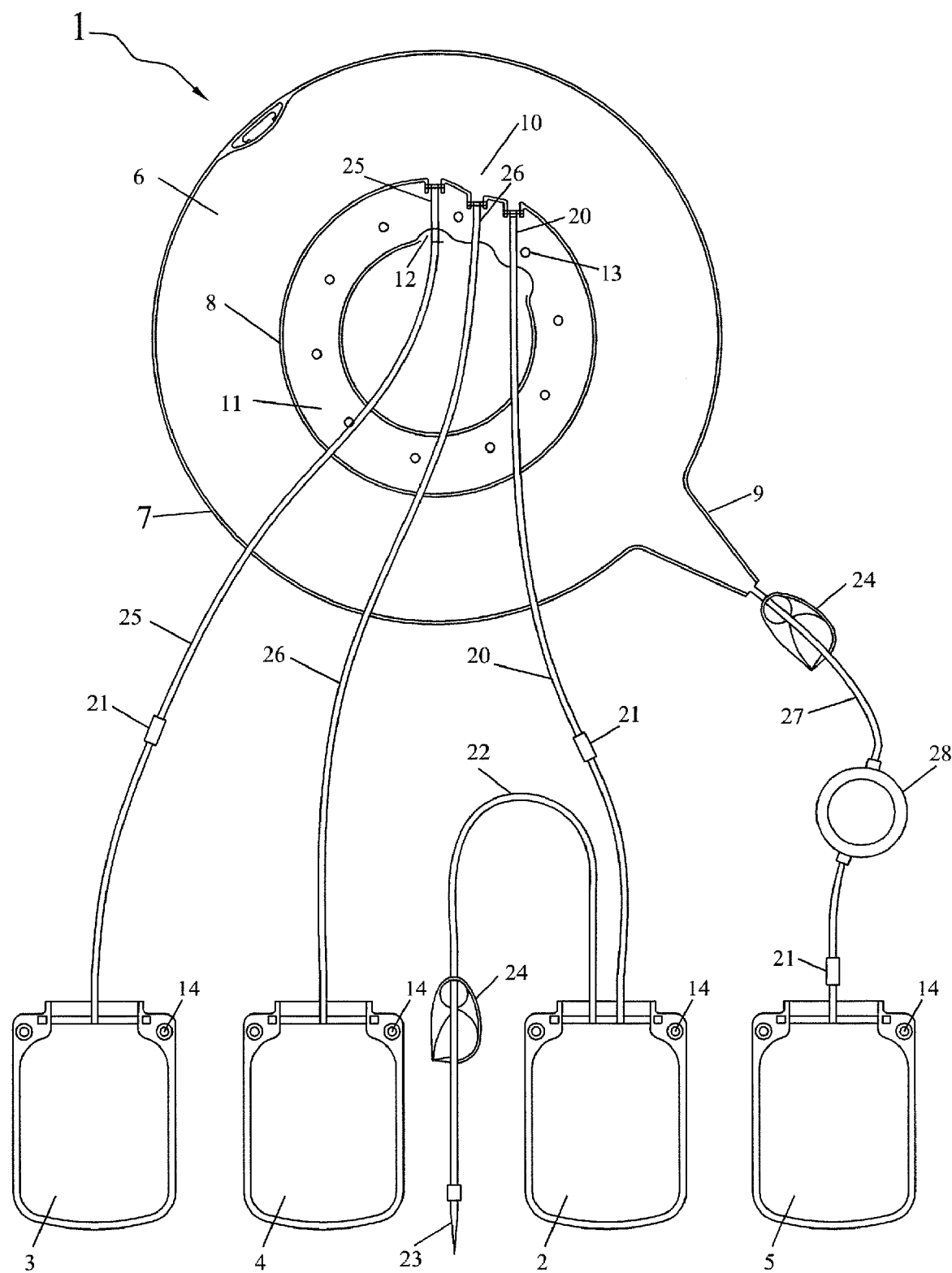
FIG. 1 is a schematic view of a set of bags designed for cooperating with a separation apparatus according to the invention.
Figure 2:
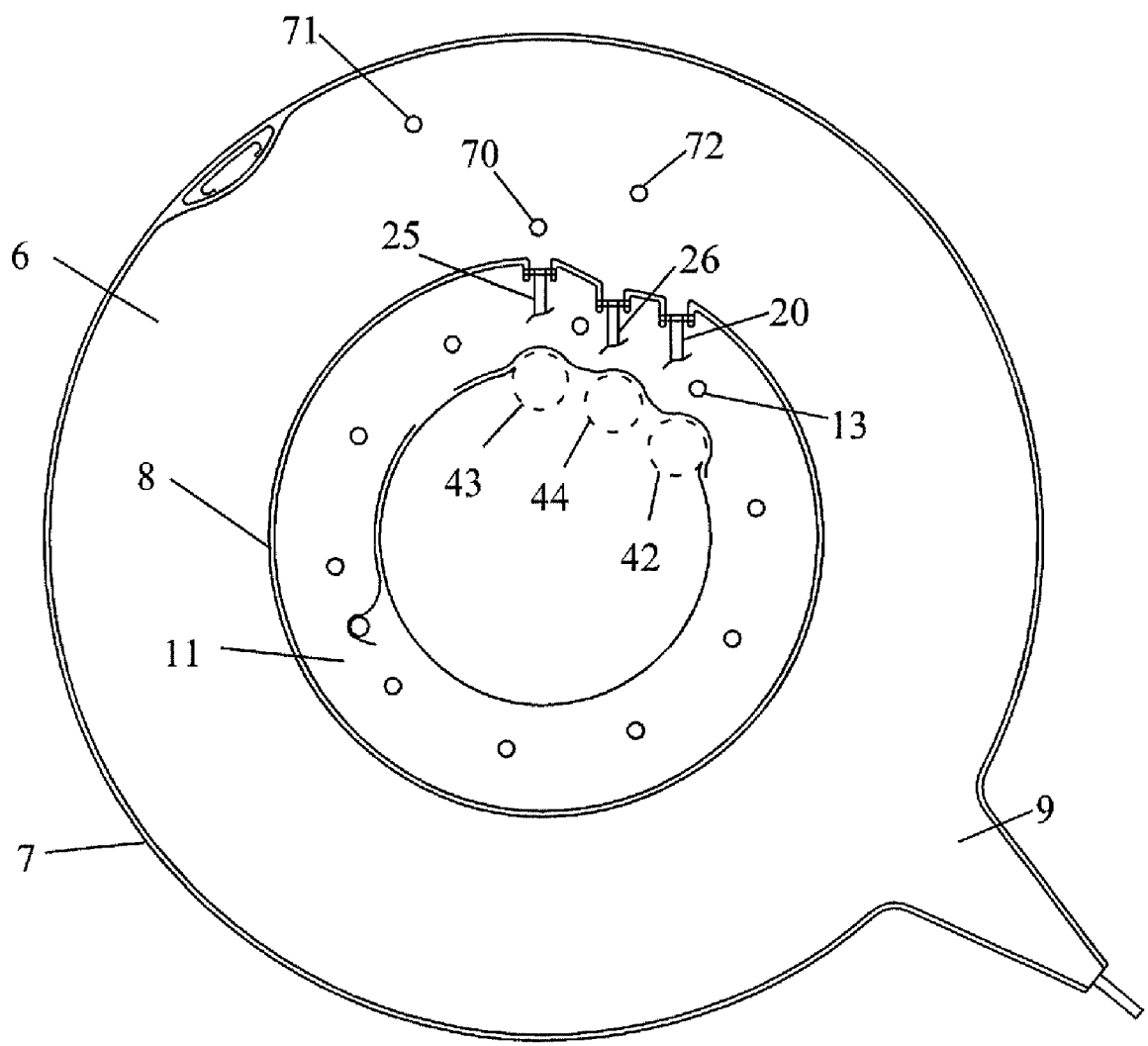
FIG. 2 is an enlarged view of the separation bag of the set of bags of FIG. 1.

FIGS. 1 and 2 show an example of a set of bags adapted to the separation of whole blood into a plasma component (essentially comprising plasma) and a red blood cell component (essentially comprising red blood cells), or into a plasma component, a red blood cell component, and an intermediate component comprising platelets and mononuclear cells. This bag set comprises a flexible separation bag 1 and four flexible satellite bags 2, 3, 4, 5 connected thereto. The separation bag 1 comprises an annular separation chamber 6 having generally circular outer and inner edges 7, 8. The outer circular edge 7 and the inner circular edge 8 of the separation chamber 6 are substantially concentric. The separation chamber 6 comprises a first, acute-angled, funnel-like extension 9 protruding outwardly from its outer edge 7 for helping drain a content of the separation chamber 6 into the fourth satellite bag 5. The separation chamber 6 also comprises a second, obtuse-angled, funnel-like extension 10 protruding from the inner edge 8, towards the center of the bag 1, for helping funnel separated components into the first, second and third satellite bags 2, 3, 4.

The separation bag 1 further comprises a semi-flexible disk-shaped connecting element 11 that is connected to the inner edge 8 of the annular chamber 5. The disk-shaped connecting element 11 comprises three rounded recesses 12 on its inner edge facing the second funnel-like extension 10, for partially surrounding three pinch valve members 42, 43, 44 of a rotor of a centrifuge to be described later (diagrammatically shown in doted line in FIG. 2). The disk-shaped connecting element 11 comprises a series of holes 13 for connecting the separation bag 1 to the rotor of a centrifuge.

The first satellite bag 2 has two purposes, and is successively used as a whole blood collection bag and as an intermediate component bag (first separation protocol, to be described later) or as a whole blood collection bag and as a waste bag (second separation protocol, to be described later). The first satellite bag 2 is intended for initially receiving a volume of whole blood from a donor (usually about 450 ml) before the separation process, and, during the separation process, either the intermediate component (first separation protocol) or a waste mixture of intermediate component and used wash solution (second separation protocol). The first satellite bag 2 is flat, substantially rectangular, and comprises two reinforced ears at its upper corners having holes 14 for hanging the bag. It is connected to the separation bag 1 by a first transfer tube 20 having a first end connected to the upper edge of the first satellite bag 2 and a second end connected to the second funnel-like extension 10, close to the inner circular edge 8. The first satellite bag 2 contains a volume of anti-coagulant solution (typically about 63 ml of a solution of citrate phosphate dextrose for a blood donation of about 450 ml). A frangible connector 21 mounted on the transfer tube 20 blocks a liquid flow through the first transfer tube 20 and prevents the anti-coagulant solution from flowing from the first satellite bag 2 into the separation bag 1.

The bag set further comprises a collection tube 22 that is connected at one end to the upper edge of the first satellite bag 2 and comprises, at the other end, a needle protected by a sheath 23. The collection tube 22 is fitted with a clamp 24.

The second satellite bag 3 is intended for initially containing a predetermined volume of wash solution for red blood cells. In a first separation protocol, the second satellite bag 3 is also used during the separation process to collect used wash solution. The second satellite bag 3 is flat, substantially rectangular, and comprises two reinforced ears at its upper corners having holes 14 for hanging the bag. It is connected by a second transfer tube 25 to the separation bag 1. The second transfer tube 25 has a first end connected to the upper edge of the second satellite bag 3 and a second end connected to the second funnel-like extension 10, close to the inner circular edge 8, opposite the second end of the first transfer tube 20 with respect to the tip of the second funnel-like extension 10. A frangible connector 21 mounted on the transfer tube 25 blocks a liquid flow through the second transfer tube 25 and prevents the wash solution from flowing from the second satellite bag 3 into the separation bag 1.

The third satellite bag 4 is intended for receiving a plasma component. It is flat, substantially rectangular, and comprises two reinforced ears at its upper corners having holes 14 for hanging the bag. It is connected by a third transfer tube 26 to the separation bag 1. The third transfer tube 26 has a first end connected to the upper edge of the third satellite bag 4 and a second end connected to the tip of the second funnel-like extension 10.

The fourth satellite bag 5 is intended for receiving a red blood cell component. It is flat, substantially rectangular, and comprises two reinforced ears at its upper corners having holes 14 for hanging the bag. It is connected by a fourth transfer tube 27 to the separation bag 1. The fourth transfer tube 27 has a first end connected to the upper edge of the fourth satellite bag 5 and a second end connected to the tip of the first funnel-like extension 9. It comprises two tube segments respectively connected to the inlet and the outlet of a leuko-reduction filter 28. The tube segment connected to the separation bag 1 is fitted with a clamp 24. The tube segment connected to the fourth satellite bag 5 is fitted with a frangible connector 21, which, when broken, allows a flow of liquid between the separation bag 1 and the fourth satellite bag 5. The filter may be, for example, a filter of the type RC2D manufactured by Pall Corporation. Such a filter comprises a disk-shaped casing to which radial inlet and outlet ports are connected, in diametral opposition. The casing, which is made of polycarbonate (GE Lexan LEXAN® polycarbonate HF 1140), has an internal volume of about 33 ml. It is filled up with a filtering medium composed of multiple layers of a non-woven web of polyester fibers (about two micron diameter). The fourth satellite bag 5 contains a volume of storage solution for red blood cells.

Variations of the separation bag 1 may include a separation chamber 6 having an outer circular edge 7 and/or an inner circular edge 8 that are eccentric; a separation chamber 6 comprising a radial wall extending from the inner edge 8 to the outer edge 7 so that the chamber 6, instead of being annular, is C-shaped. The separation chamber 6 may have any shape including an inner edge and an outer edge (the inner edge being closer to the axis of the rotor of a centrifuge than the outer edge, when the separation bag is mounted on the rotor of a centrifuge), for example the shape of a portion of annulus delimited by two lateral radial edge or a rectangular shape. In this variation, all the satellite bags may be connected to the inner edge of the separation bag.

Also, the separation bag 1 can be shaped so as to fit either on a flat support surface or on a frusto-conical support surface of the rotor of a centrifuge The bags and the tubes of the bag set shown in FIGS. 1 and 2 are all made of flexible plastic material appropriate to contact blood and blood components.

Figure 3:
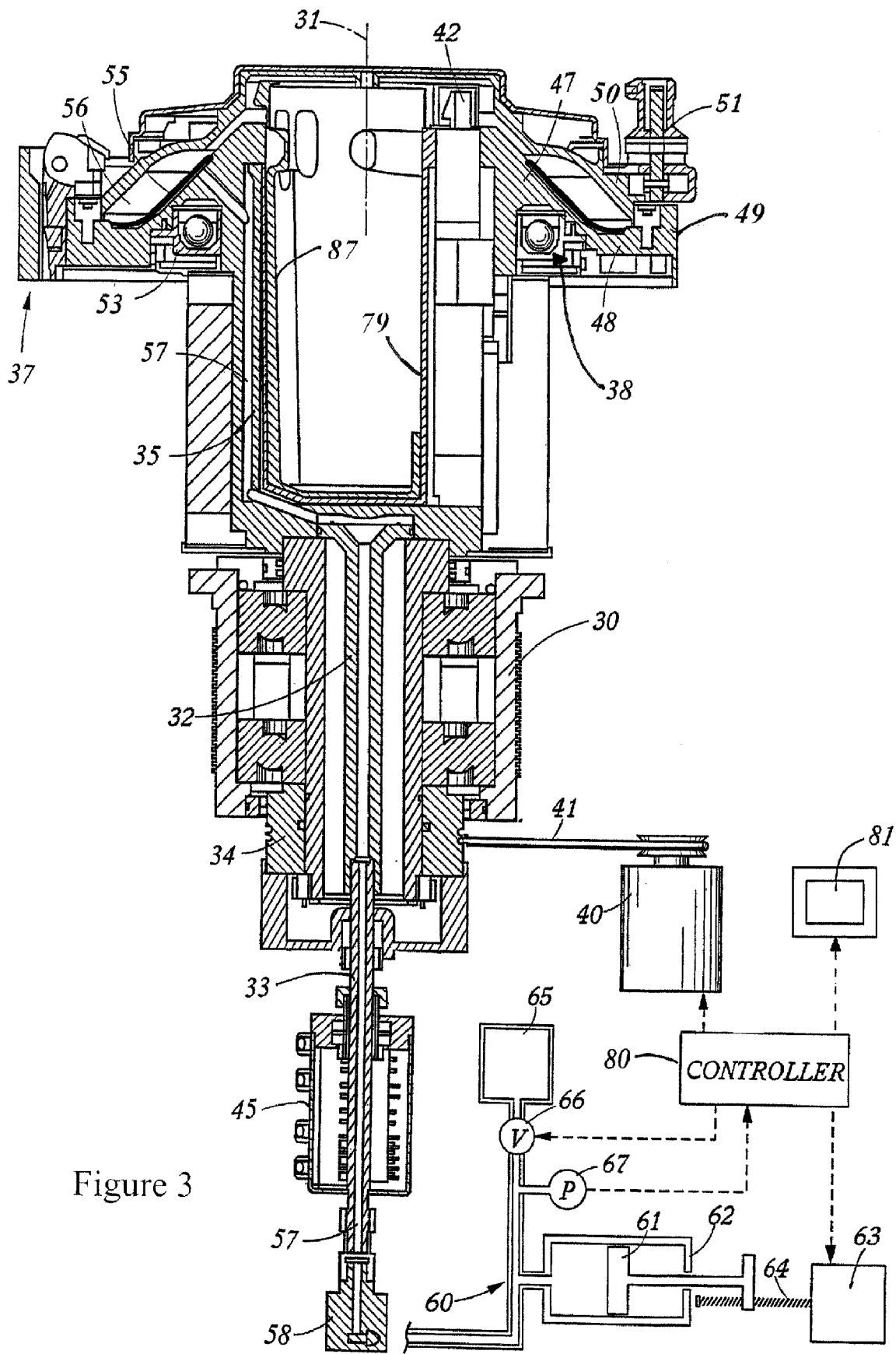
FIG. 3 is a schematic view, partly in cross-section, of a separation apparatus according to the invention.
Figure 4:
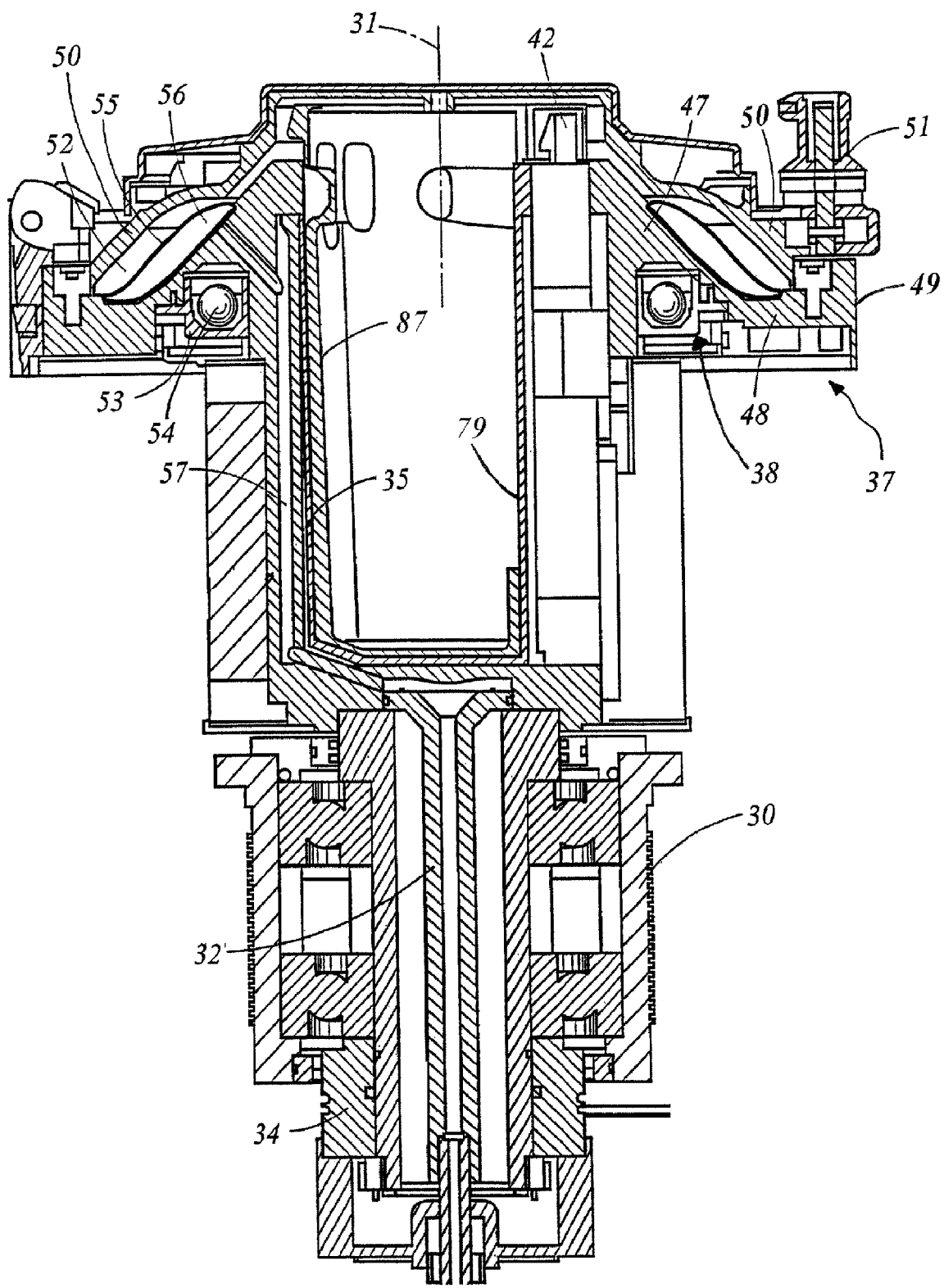
FIG. 4 is a cross-section view of the rotor of a separation apparatus according to the invention.
Figure 5:
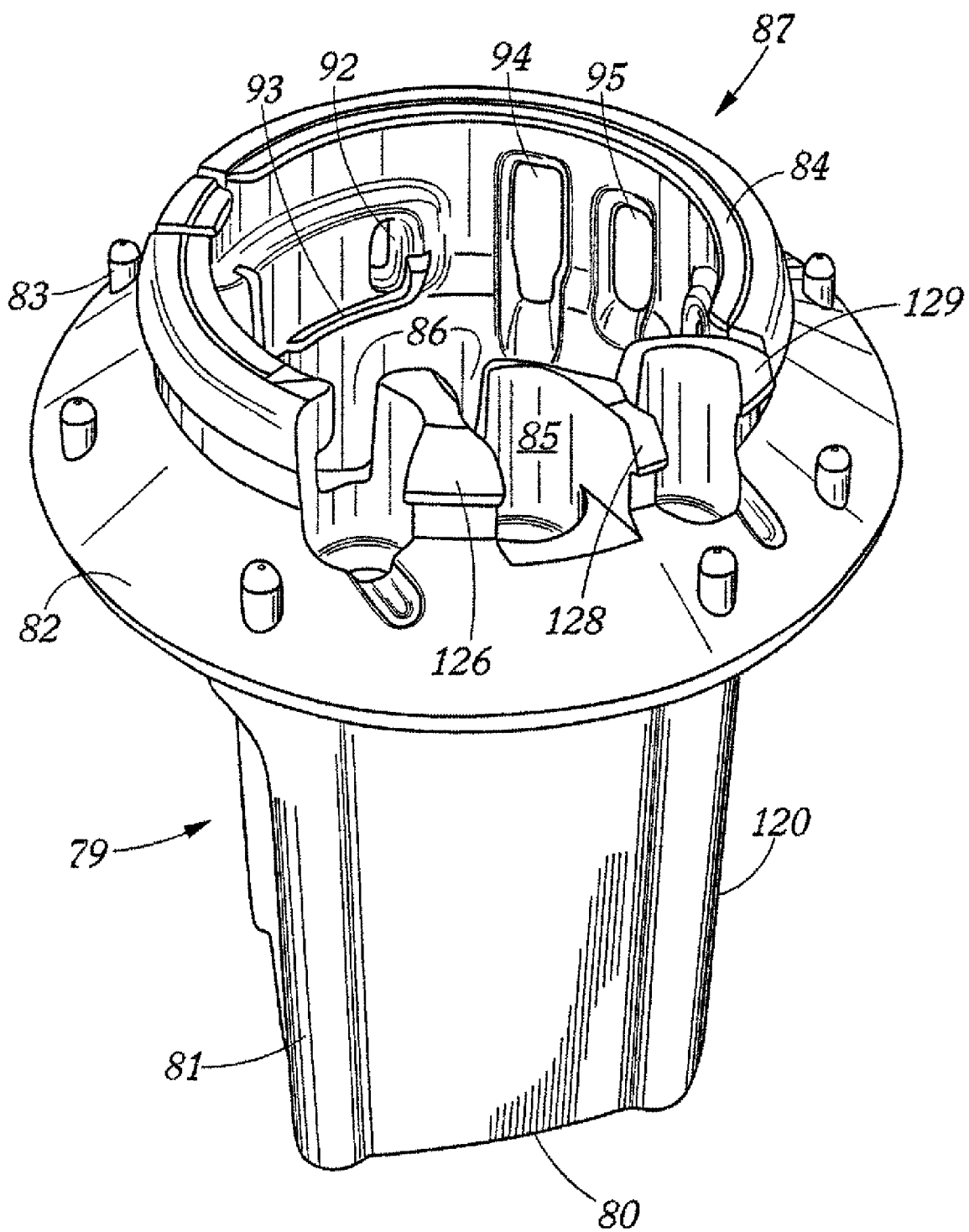
FIG. 5 is a perspective view of a first embodiment of a rotor liner and bag loader assembly fitting within the rotor of FIG. 4.
Figure 6:
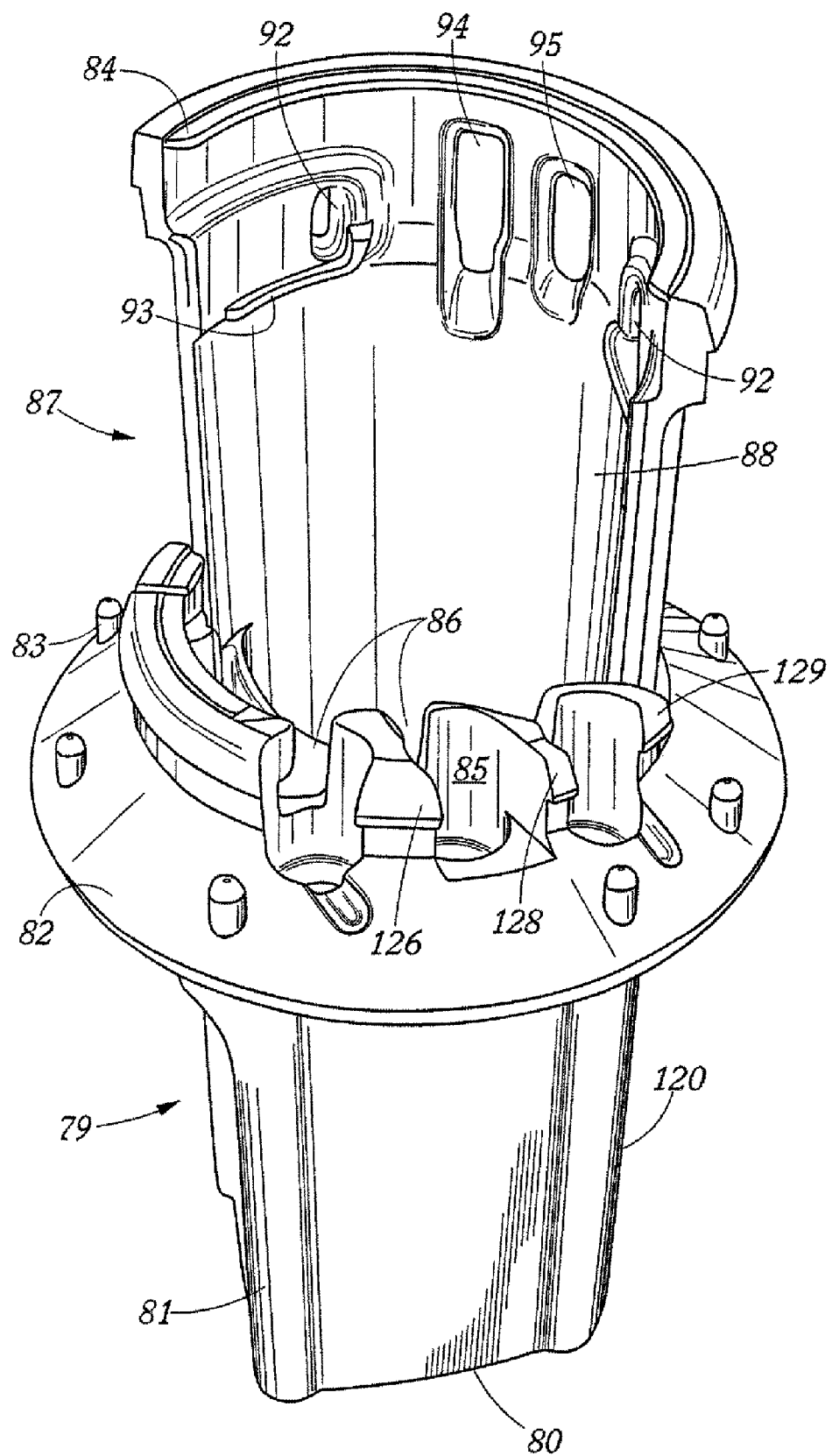
FIG. 6 is a perspective view of the rotor liner and bag loader assembly of FIG. 5, in which a bag loader is shown partially lifted.
Figure 7:
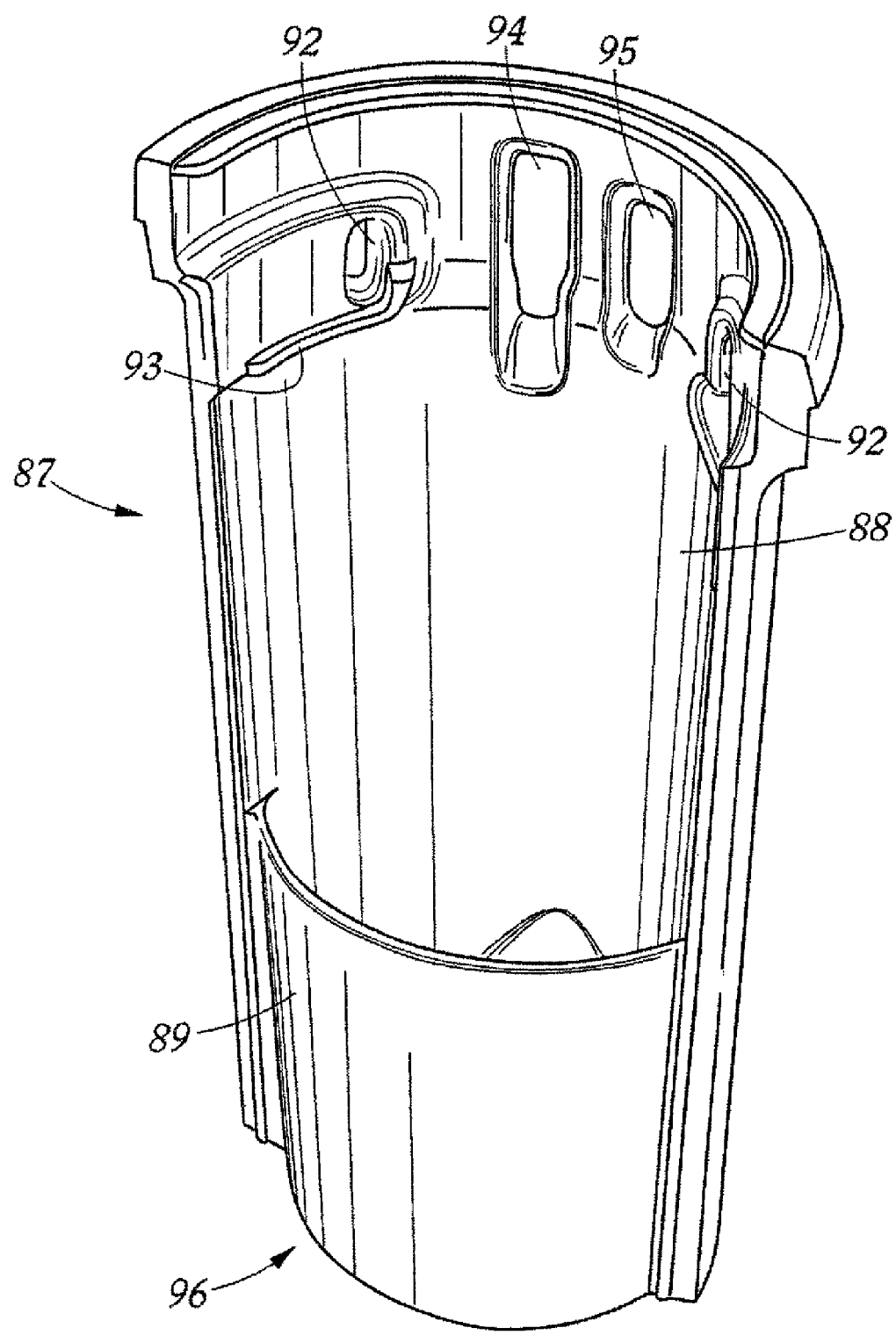
FIG. 7 is a perspective view of the bag loader of FIG. 6.
Figure 8:
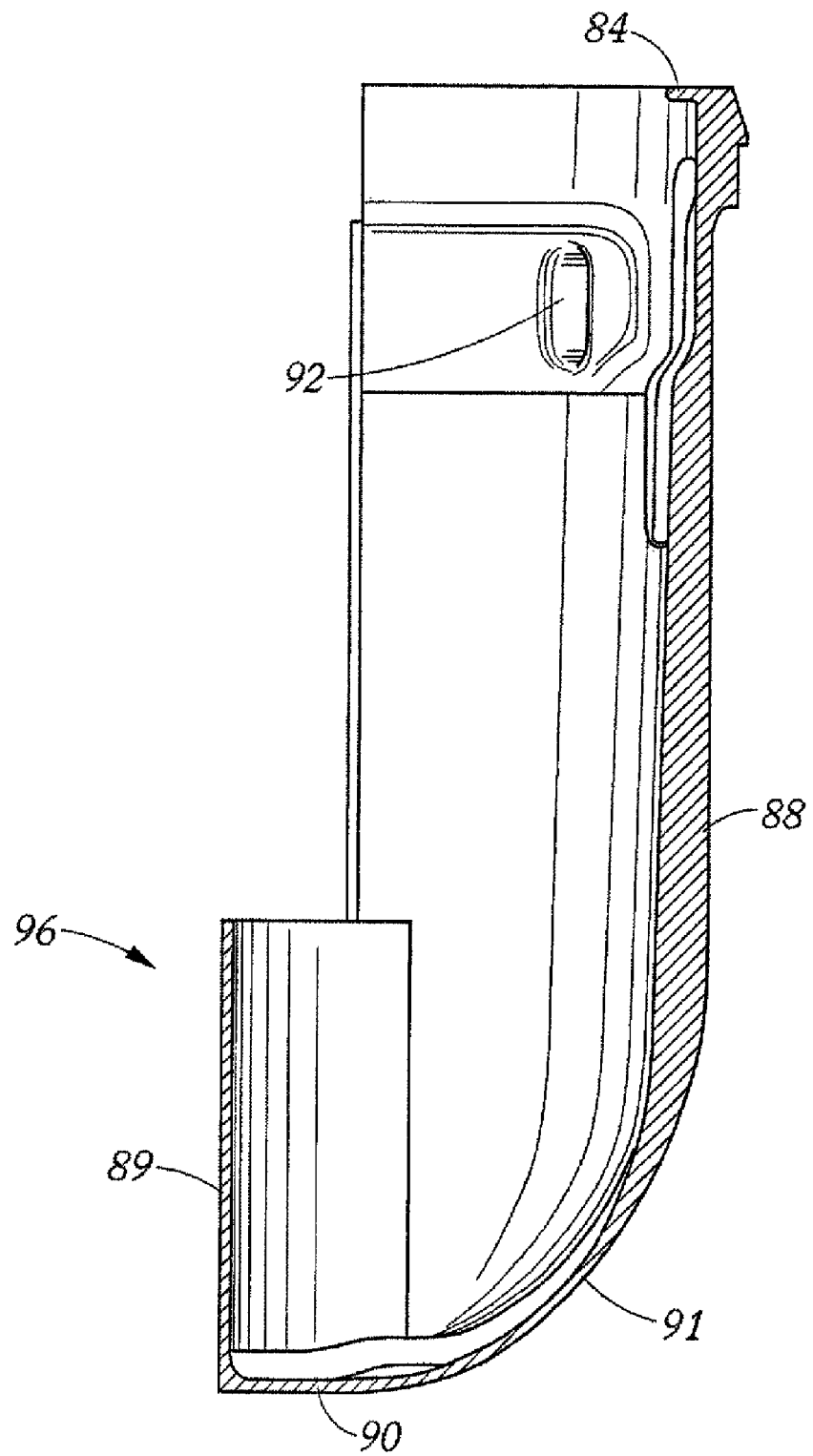
FIG. 8 is a cross section view of the bag loader of FIG. 7, along a vertical plane.

FIGS. 3 and 4 show an embodiment of an apparatus for separating a volume of composite liquid by centrifugation. The apparatus comprises a centrifuge adapted for receiving the set of separation bags shown in FIGS. 1 and 2, and a component transferring mechanism for causing the transfer of separated components into the satellite bags.

The centrifuge comprises a rotor that is supported by a bearing assembly 30 allowing the rotor to rotate about a vertical central axis 31. The rotor comprises a cylindrical rotor shaft comprising a first upper portion 32 and a second lower portion 33 wherein the upper portion 32 of the shaft extends in part through the bearing assembly 30 and a pulley 34 is connected to the lower end of the upper portion 32 of the shaft; a central compartment 35 for containing satellite bags, which is connected to the rotor shaft 32, 33 at the upper end thereof; and a rotor liner 79 fitting within the central compartment 35 and a movable bag loader 87 for supporting at least one satellite bag in a determined position within the central compartment 35; a circular turntable 37 for supporting a separation bag, which is connected to the compartment 35 at the upper end thereof, the central axes of the rotor shaft 32, 33, the compartment 35 and the turntable 37 coinciding with the rotation axis 31; and a balancing assembly 38, which is secured to the turntable 37.

The centrifuge further comprises a motor 40 coupled to the rotor by a belt 41 engaged in a groove of the pulley 34 so as to rotate the rotor about the central vertical axis 31.

The separation apparatus further comprises a first, second and third pinch valve members 42, 43, 44 that are mounted on the rotor for selectively blocking or allowing a flow of liquid through a flexible plastic tube, and selectively sealing and cutting a plastic tube. Each pinch valve member 42, 43, 44 comprises an elongated cylindrical body and a head having a groove that is defined by a stationary upper jaw and a lower jaw movable between an open and a closed position, the groove being dimensioned so that one of the transfer tubes 20, 25, 26 of the bag sets shown in FIGS. 1 and 2 can be snuggly engaged therein when the lower jaw is in the open position. The elongated body contains a mechanism for moving the lower jaw and it is connected to a radio frequency generator that supplies the energy necessary for sealing and cutting a plastic tube. The pinch valve members 42, 43, 44 are mounted at the periphery of the central compartment 35 so that their longitudinal axes are coplanar, and parallel to the central axis 31 of the rotor, and their heads protrude above the rim of the central compartment 35. The position of the pinch valve members 42, 43, 44 with respect to the separation bag 1 and the transfer tubes 20, 25, 26 connected thereto when the separation bag 1 is mounted on the turntable 37 is shown in doted lines in FIG. 2. Electric power is supplied to the pinch valve members 42, 43, 44 through a slip ring array 45 that is mounted around the lower portion 33 of the rotor shaft.

The turntable 37 comprises a central frusto-conical portion 47, the upper, smaller edge of which is connected to the rim of the compartment 35, an annular flat portion 48 connected to the lower, larger edge of the frusto-conical portion 47, and an outer cylindrical flange 49 extending upwards from the outer periphery of the annular portion 48. The turntable 37 further comprises a vaulted circular lid 50 that is secured to the flange 49 by a hinge so as to pivot between an open and a closed position. The lid 50 is fitted with a lock 51 by which it can be blocked in the closed position. The lid 50 has an annular interior surface that is so shaped that, when the lid 50 is in the closed position, it defines with the frusto-conical portion 47 and the annular flat portion 48 of the turntable 37, a frusto-conical annular compartment 52 having a radial cross-section that has substantially the shape of a parallelogram. The frusto-conical annular compartment 52 (later the "separation compartment"), which has a fixed volume, is intended for containing the separation bag 1 shown in FIGS. 1 and 2.

The balancing assembly 38, which has generally the shape of a ring, is mounted on the rotor within the space that extends between the upper end of the central compartment 35 and the frusto-conical wall 47 of the turntable 37. The balancing assembly 38 comprises a ring-shaped housing 53 defining a cavity whose cross-section, along a radial plane, is generally rectangular. The balancing assembly further comprises a plurality of ponderous balls 54 having a diameter that is slightly less than the radial depth of the cavity of the housing 53. When the balls 54 are in contact with each other they occupy a sector of the housing 52 of about 180 degrees.

The component transferring mechanism comprises a squeezing system for squeezing the separation bag within the separation compartment 52 and causing the transfer of separated components into the satellite bags. The squeezing system comprises a flexible annular diaphragm 55 that is so shaped as to line the frusto-conical portion 47 and the annular flat portion 48 of the turntable 37, to which it is secured along its smaller and larger circular edges. The squeezing system further comprises a hydraulic pumping station 60 for pumping a hydraulic liquid in and out an expandable hydraulic chamber 56 defined between the flexible diaphragm 55 and the turntable 37, via a duct 57 extending through the rotor from the lower end of the lower portion 33 of the rotor shaft to the turntable 37. The pumping station 60 comprises a piston pump having a piston 61 movable in a hydraulic cylinder 62 fluidly connected via a rotary fluid coupling 58 to the rotor duct 57. The piston 61 is actuated by a stepper motor 63 that moves a lead screw 64 linked to the piston rod 62. The stepper motor 63 can be controlled by discrete increments or steps, each step corresponding to a fraction of turn of the axle of the motor 63, corresponds to a small linear displacement of the piston 61 and also to a small determined volume of liquid being pumped in or out of the hydraulic chamber 56. The hydraulic cylinder 62 is also connected to a hydraulic liquid reservoir 65 having an access controlled by a valve 66 for selectively allowing the introduction or the withdrawal of hydraulic liquid into and from a hydraulic circuit including the hydraulic cylinder 62, the rotor duct 57 and the expandable hydraulic chamber 56. A pressure gauge 67 is connected to the hydraulic circuit for measuring the hydraulic pressure therein.

The separation apparatus further comprises three sensors 70, 71, 72 for detecting characteristics of the separation process occurring within a separation bag 1 when the apparatus operates. The three sensors 70, 71, 72 are embedded in the lid 50 at different distances from the rotation axis 31 of the rotor, a first sensor 70 being the closest to the rotation axis 31, a second sensor 71 being the farthest to the rotation axis 31 and a third sensor 72 occupying an intermediate position. When the lid 50 is closed, the three sensors 70, 71, 72 face the separation bag 1 as shown in FIG. 2. The first sensor 70 (later the "inner sensor") is embedded in the lid 50 so as to be positioned over the separation chamber 6 at a short distance from the end of the second transfer tube 25 connected to the second funnel-like extension 10. The inner sensor 70 is able to detect an interface gas/liquid, an interface between plasma and a platelet/mononuclear cell layer, an interface between platelet rich plasma and mononuclear cells, as well as red blood cells. The second sensor 71 (later the "outer sensor") is embedded in the lid 50 so as to be positioned over the separation chamber 6 at about two third of the width of the separation chamber from the inner edge 8 thereof, and it is offset with respect to the second funnel-like extension 10, while being closer to the end of the second transfer tube 25 than to the respective ends of the first and second transfer tubes 20, 26. The outer sensor 71 is able to detect a liquid, e.g. blood. The third sensor 72 (later the "intermediate sensor") is embedded in the lid 50 so as to be positioned over the separation chamber 6 at about one third of the width of the separation chamber from the inner edge 8 thereof, substantially on the same radius as the end of the third transfer tube 26 connected to the second funnel-like extension 10. The intermediate sensor 72 is able to detect an interface between plasma and blood cells. Each sensor 70, 71, 72 can comprise a photocell including an infra-red LED and a photo-detector. Electric power is supplied to the sensors 70, 71, 72 through the slip ring array 45.

The separation apparatus further comprises a controller 80 including a control unit (microprocessor) and a memory for providing the microprocessor with information and programmed instructions relative to various separation protocols and to the operation of the apparatus in accordance with such separation protocols. In particular, the microprocessor is programmed for receiving information relative to the centrifugation speed(s) at which the rotor is to be rotated during the various stages of a separation process, and information relative to the various transfer flow rates at which separated components are to be transferred from the separation bag 1 into the satellite bags 2, 3, 4. The information relative to the various transfer flow rates can be expressed, for example, as hydraulic liquid flow rates in the hydraulic circuit, or as rotation speeds of the stepper motor 63 of the hydraulic pumping station 60. The microprocessor is further programmed for receiving, directly or through the memory, information from the pressure gauge 67 and from the photocells 70, 71, 72 and for controlling the centrifuge motor 40, the stepper motor 63, and the pinch valve members 42, 43, 44 so as to cause the separation apparatus to operate along a selected separation protocol.

The rotor further comprises a rotor liner 79 fitting within the central compartment 35, and a bag loader 87 fitting within the rotor liner, for receiving the satellite bags, the transfer tubes and a leuko-reduction filter and for holding the bags in a determined position. FIGS. 5 to 8 show an embodiment of a rotor liner 79 and a bag loader 87. One of the functions of the bag loader 87 is to serve as a bag loading mechanism for loading/unloading at least one satellite bag into/from the central compartment 35 of the rotor. One of the functions of the rotor liner 79 is to serve as a guiding mechanism for guiding the bag loader 87 within the central compartment 35 when the bag loader 87 is inserted into and removed from the central compartment 35, and for positioning the bag loader 87 in a determined position within the rotor.

The rotor liner 79 comprises a container 120 having a bottom wall 80 and a lateral wall 81, and a flange 82 that is connected to the container 120 slightly below the upper rim of the lateral wall 81.

The lateral wall 81 is substantially defined by a frustum of cone flaring upwards, which is intersected by a flat plane extending in parallel to the axis of the frustum of cone. The lateral wall 81 has therefore a first portion that is a sector of a frustum of cone, connected to a second portion that is flat and has the shape of a parallelogram. The axis of the frustum of cone partially defining the first portion of the lateral wall 81 (which forms also a longitudinal axis of the rotor liner 79) coincides with the rotation axis 31 of the rotor. The angle of the frustum of cone is about 3 degrees. It could be more open. However, the larger the angle, the smaller the space available inside the rotor liner 79 for storing satellite bags.

The upper rim of the lateral wall 81 is inwardly bent over about two thirds of its circumference so as to form a narrow circular lip 84 underneath which loops of tube can be stuck. The lip 84 extends in a plane that is substantially perpendicular to a longitudinal axis of the rotor liner 79.

The flange 82 is annular and has the shape of a frustum of cone flaring downwards at an angle of about 85 degrees. A series of rounded pins 83 arranged on a circle protrude upwards from the flange 82. The size and the location of the pins 83 correspond to the size and location of the holes 13 in the semi-flexible disk-shaped connecting element 11 of a separation bag 1. The pins 83 help position the separation bag 1 on the rotor, and prevent the separation bag 1 from moving with respect to the rotor when the rotor is rotating. Along the flat portion of the lateral wall 81 of the rotor liner 79, the flange 82 comprises three aligned cylindrical apertures 85 that encroach in part on the adjacent flat wall. When the rotor liner 79 is fully inserted in the central compartment 35 of a rotor, the three pinch valve members 42, 43, 44 extend through the apertures 85 so that the heads of the pinch valve members protrude above the flange 82. Three guiding elements 126, 128, 129 of somewhat complex geometrical shapes protrude along the inner periphery of the flange 82, partially surround the three apertures 85, and delimit three narrow gates 86 by which tubes engaged in the pinch valve members 42, 43, 44 can be guided into the central compartment 35 along determined directions.

The bag loader 87 is dimensioned so as to fit within the rotor liner 79, and to form, when it is fully engaged therein, a support member for supporting at least one satellite bag full of a liquid and holding it in such a way that the content of the satellite bag is fully transferred into a separation bag connected to the satellite bag when the rotor is rotated at a selected speed. The support member is so designed that a satellite bag secured thereto has a lower portion that is closer to the rotation axis 31 of the rotor that an upper portion thereof to which a transfer tube is connected.

The support member comprises a portion of wall that is tilted with respect to the rotation axis 31 of the rotor. A satellite bag secured by an upper portion thereof to an upper part of the tilted wall is pressed against the tilted wall by centrifugation forces during rotation of the rotor so that a lower portion of the satellite bag is closer to the axis of rotation than an upper portion thereof.

The bag loader 87, generally comprises an upper part comprising a securing mechanism for removably securing an upper portion of at least one satellite bag to the bag loader 87; a lower part comprising a receptacle for containing a lower portion of at least one satellite bag; and an intermediate part connecting the upper part to the lower part and exposing an intermediate portion of a satellite bag having an upper part secured to the upper part of the bag loader 87 and a lower part inserted in the receptacle.

In more detail, the loader 87 has a first outer, gutter-like, wall 88, which extends over the height of the rotor liner 79, and a second inner, gutter-like, wall 89, which extends from the bottom of the bag loader over about one third of the eighth of the rotor liner 79. The inner and outer walls 88, 89 are connected along their lateral edges so that the concavity of the inner wall 89 faces the concavity of the outer wall 88. The inner surface first outer wall 88 is defined by a sector of a frusto-conical wall whose angle is about 3 degrees. The bag loader 87 has a longitudinal axis that coincides with the central axis of the frustum of cone that defines the inner surface of the outer wall 88. When the bag loader 87 is fully inserted in the central compartment 35 of a rotor, the longitudinal axis of the bag loader 87 coincides with the rotation axis 31 of the rotor. The second inner wall 89 is a sector of a cylinder having a longitudinal axis parallel to the longitudinal axis of the bag loader 87. The dimensions of the two walls 88, 89 and the distance between them is so selected that the distance between any point of the inner wall 89 to the longitudinal axis of the bag loader 87 is less than the distance from the longitudinal axis to the point (recesses 94, 95) of the outer wall 88 where the inlet/outlet of a satellite bag secured to the outer wall 88 is located. This helps ensure that satellite bags attached to a bag loader are confined in an area of a rotor where, under centrifugation forces, the whole content of a satellite bag can be transferred to a separation bag connected thereto. The bag loader 87 further comprises a bottom wall having a flat portion 90, perpendicular to the its longitudinal axis, which is connected to the lower rim of the second inner wall 89 (sector of cylinder) and a curved ogival portion 91, which raises from the flat portion 90 to a point located on a median longitudinal axis of the first outer wall 88 (sector of frustum of cone), at about one fifth of the height of the bag loader 87, from the flat bottom portion 90. In geometrical terms, the second portion 91 of the bottom of the bag loader 87 results from the intersection of a frustum of cone and of a cylinder having perpendicular axes. The second inner wall 89, the lower portion of first outer wall 88 that is connected to the second inner wall 89, and the bottom wall 90, 91 connected thereto, form a receptacle 96 for a lower portion of satellite bags attached to the bag loader 87. This receptacle facilitates the insertion of the bag loader 87 within the central compartment 34 of a rotor by preventing the lower portion of the satellite bags from interacting with the inner surface of the rotor liner 79.

The bag loader 87 further comprises a securing mechanism in its upper part, including two lateral recesses 92 opening on its inner surface, for removably receiving and locking the ends of complementary locking elements of a bag holder 100 to be described later. A guide 93, in the form of a narrow tongue, extends from the bottom of each recess 92 towards the lateral edges of the bag loader 87 for helping set the bag holder 100 in place. Between the two locking recesses 92, the bag loader 87 comprises two other recesses 94, 95 for accommodating the end of transfer tubes embedded in an upper portion of a satellites bag.

Figure 9:
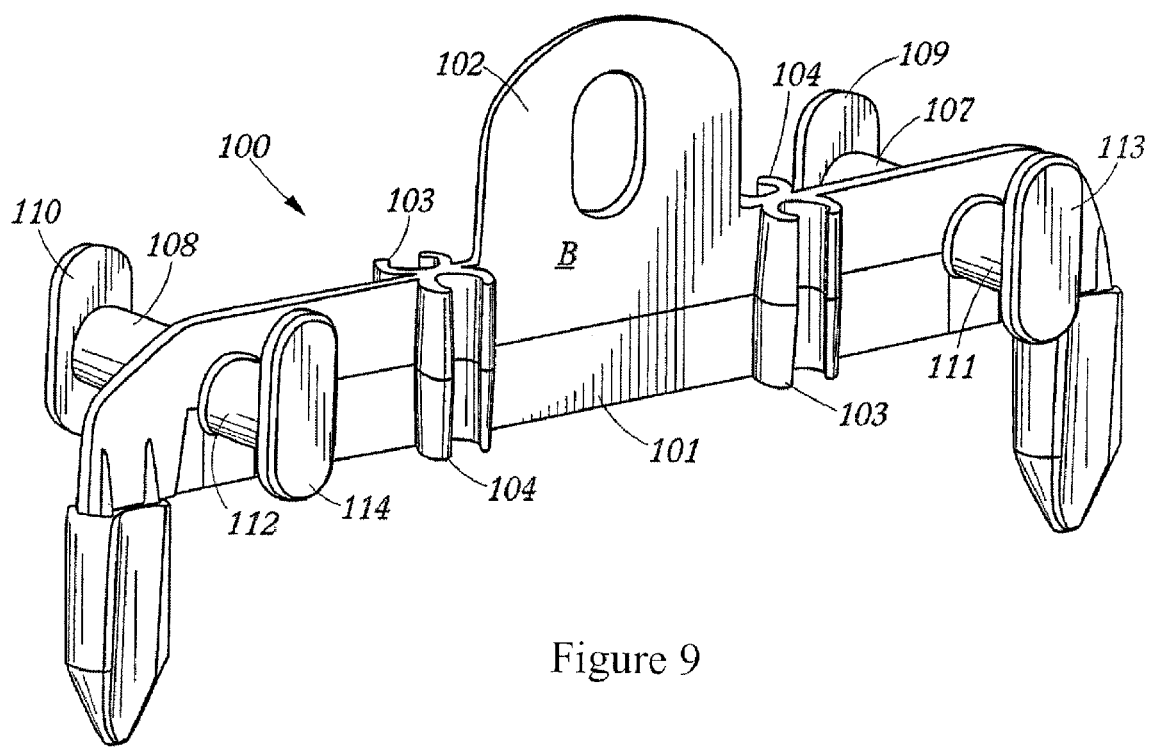
FIGS. 9 and 10 are perspective views of a bag holder fitting in the bag loader of FIGS. 6 to 8.
Figure 10:
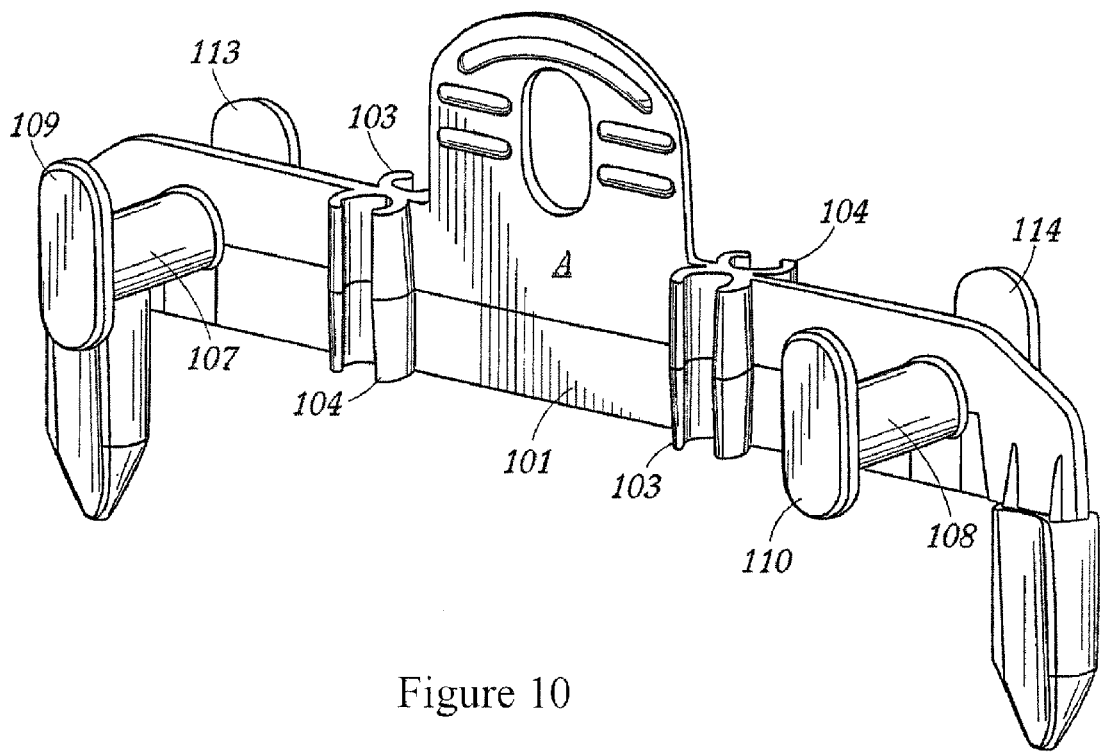

The bag holder 100 shown in FIGS. 9 and 10 is used for securing the satellite bags 2, 3, 4 to the loader 87 in a determined position during the operation of the centrifuge.

The bag-holder 100 comprises an elongated flat body 101 in the middle of which a flat U-shaped handling appendage 102 is connected so as to protrude upwards when the bag-holder 100 is mounted in the bag loader 87. The elongated flat body 101 is fitted on both sides A and B with two parallel gutter-like guides 103, 104 that are perpendicular to a longitudinal axis of the elongated flat body 101 and extend in a central portion of the elongated flat body 101, substantially in alignment with the lateral edges of the U-shaped handling appendage 102, respectively. When the bag holder 100 is secured to the bag loader 87, the elongated flat body 101 is substantially perpendicular and the gutter-like guides 103, 104 are substantially parallel to the rotation axis 31 of the rotor. The gutter-like guides 103, 104 are so dimensioned that a portion of transfer tube 20, 25, 26 or a needle sheath 23 can be snuggly engaged therein.

The bag-holder 100 further comprises a hanging mechanism in the form of a first couple of pegs 107, 108 connected to the elongated flat body 101 for hanging at least one satellite bag 2, 3, 4, 5 in the loader 87. The pegs 107, 108 extend perpendicularly from the side A of the elongated flat body 101. The distance between the two pegs 107, 108 is substantially the same as the distance between the holes 14 in the ears of the satellite bags 2, 3, 4, 5. The cross-section of the pegs 107, 108 substantially fits in the holes 14.

The pegs 107, 108 are also used to secure the bag holder 100 to the loader 87. To this end, the distance between the two pegs 107, 108 is substantially the same as the distance between the two locking recesses 92 in the upper part of the loader 87. Also, the tip of each peg 107, 108 is fitted with a locking element 109, 110 that can removably lock within a locking recess 92 of the loader 87. Each locking element 109, 110 is comprised of a flexible plate having rounded ends, which is perpendicularly connected to the corresponding pegs 107, 108.

The bag-holder 100 further comprises a second couple of pegs 111, 112 connected to the elongated flat body 101 for releasably securing a separation bag 1 and, as the case may be, a satellite bag 2, 3, 4, 5 thereto. The pegs 111, 112 extend perpendicularly from the side B of the elongated flat body 101 along the same axis as the pegs 107, 108. The tips of the pegs 111, 112 are fitted with retaining elements 113, 144 for preventing a satellite bag engaged on the pegs from escaping therefrom during centrifugation of the bag assembly. Overall, the second couple of pegs 111, 112 is identical to the first couple of pegs 107, 108 save for the length of the pegs, which is longer in the first couple than in the second couple.

It results from the respective arrangement of the elongated flat body 101 and the first and second couple of pegs 106, 107, 111, 112 that satellite bags 2, 3, 4, 5 engaged on the pegs occupy a determined position in the central compartment 35 of a rotor when the bag loader 87 is fully engaged in the rotor liner 79. Moreover, when the rotor starts rotating, a satellite bag full of liquid mounted in the bag loader 87 by mechanism of the first couple of pegs 106, 107 is stuck by centrifugation forces onto the frusto-conical wall 88 and the rounded bottom part 91 of the loader 87 so that the upper part of the bag is farther apart from the rotation axis 31 of the rotor than the lower part of the bag. Thanks to this disposition, when the transfer tube connecting the satellite bag to the separation bag is open and the rotation speed is high enough, the liquid initially contained in the satellite bag wholly drains into the separation bag.

An example of a first separation protocol aimed at the preparation of three blood components from a whole blood donation, namely a plasma component, a platelet/mononuclear cell component and a washed red blood cell component, is described below.

The operation of the separation apparatus along the first separation protocol is as follows:

First stage (first protocol): a bag set as shown in FIGS. 1, 2 is set in place in the rotor of a centrifuge (as shown in FIGS. 3, 4).

At the onset of the first stage, the first satellite bag 2 of the bag set of FIG. 1 contains a volume of anti-coagulated whole blood (usually about 500 ml) and the second satellite bag 3 contains a volume of wash solution (about 350 ml of saline solution). The collection tube 22 has been sealed and cut. The clamp 24 on the transfer tube 27 connecting the fourth satellite bag 5 to the separation bag 1 is closed. The first satellite bag 2 and the second satellite bag 3 are engaged on the first couple of pegs 107, 108 of a bag holder 100 (as shown in FIGS. 9-10), the first satellite bag 2 being engaged first. The third satellite bag 4 and the fourth satellite bag 5 are engaged on the second couple of pegs 111, 112. The satellite bags 2, 3, 4, 5 are inserted in a bag loader 87 and the bag holder 100 is secured to the bag loader 87 by forcibly engaging the flexible locking elements 109, 110 of the bag holder 100 into the locking recesses 92 of the bag holder 87, as a result of which the first satellite bag 2 is adjacent to the inner surface of the bag loader 87. The bag loader 87 is then fully inserted into the central compartment 35 of the centrifuge, in which it guided by the rotor liner 79. The satellite bags 2, 3, 4, 5 are then substantially located on one side of a plane containing the rotation axis of the rotor 31.

The separation bag 1 is laid on the turntable 37 and the pins 83 on the flange 82 of the rotor liner 79 are engaged in the holes 13 of the disk-shaped connecting element 11 of the separation bag 1. The first transfer tube 20 connecting the first satellite bag 2 to the separation bag 1 is engaged in the first pinch valve member 42, the second transfer tube 25 connecting the second satellite bag 3 to the separation bag 1 is engaged in the second pinch valve member 43, and the third transfer tube 26 connecting the third satellite bag 4 to the separation bag 1 is engaged in the third pinch valve member 44. The frangible pins 21 blocking communication between the first satellite bag 2 and the separation bag 1 and between the second satellite bag 3 and the separation bag 1 are broken. The lid 49 of the rotor is closed.

Second stage (first protocol): the anti-coagulated whole blood contained in the first satellite bag 2 is transferred into the separation bag 1.

At the onset of the second stage, the first pinch valve member 42 is open and the second and third pinch valve members 43, 44 are closed. The rotor is set in motion by the centrifuge motor 40 and its rotation speed increases steadily until it reaches a first centrifugation speed (e.g. about 1500 RPM) that is so selected as:
  to be high enough to cause the transfer, under centrifugation forces, of the content of the first satellite bag 2 into the separation bag 1;
  to be high enough to cause the whole transfer to happen in the shorter period of time;
  while, at the same time,
  to be low enough not to cause pressure within the first satellite bag 2 to substantially exceed a determined pressure threshold above which hemolysis would occur;
  to be low enough not to generate shearing forces in the flow of blood entering the separation bag 1 that would cause hemolysis.

It has been determined that the pressure threshold above which hemolysis occurs in the satellite bag 2 is about 10 PSI, and that the maximum rotation speed at which such pressure threshold is not reached and the shearing forces in the blood flow entering the separation bag do not cause hemolysis is about 1800 RPM. At a rotation speed of about 1500 RPM, it takes about one minute for transferring about 500 ml of anti-coagulated blood from the first satellite bag 2 into the separation bag 1.

When the outer cell 71 detects blood, the valve member 44 controlling a flow of fluid through the third transfer tube 26 connected to the third satellite bag 4 (in which a plasma component will be later transferred) is opened for a predetermined amount of time (for example, about 30 seconds) so as to allow air to vent from the separation bag 1 when blood pours therein.

If the outer cell 71 has not detected blood within a predetermined period of time following the start of the centrifugation process, the control unit 80 causes the rotor to stop and an alarm to be emitted. This could happen in particular if the frangible connector 21 in the first transfer tube 20 has inadvertently not been broken.

Third stage (first protocol): the air present in the separation bag 1 is purged into the first satellite bag 2, in which a platelet/mononuclear cell component is to be later transferred.

At the onset of the third stage, the whole content of the first satellite bag 2 has been transferred into the separation bag 1, the first pinch valve member 42 is open, and the second and third pinch valve members 43, 44 are closed. The rotor rotates at the first rotation speed (about 1500 RPM). The pumping station 60 is actuated so as to pump hydraulic liquid at a constant flow rate (for example, about 240 ml/min) into the hydraulic chamber 56 and consequently squeeze the separation bag 1. The air present in the separation bag 1 is expelled into the first satellite bag 2 in which a platelet/mononuclear cell component will be later transferred. After a predetermined period of time following the detection of an interface air/liquid by the inner sensor 70, the pumping station 60 is stopped and the first pinch valve member 42 is closed.

Fourth stage (first protocol): the blood components within the separation chamber are sedimented to desired layers.

At the onset of this stage, the three pinch valve members 42, 43, 44 are closed. The speed of the rotor is increased steadily until it reaches a second, high, centrifugation speed (for example, about 3200 RPM, so-called "hard spin") at which the blood components will sediment at the desired level. The rotor is rotated at the second centrifugation speed for a predetermined period of time (for example, about 220 seconds), which is selected so that, whatever the hematocrit of the whole blood initially transferred in the separation chamber 1, the blood sediments therein at the end of the predetermined period to a point where the hematocrit of the outer annular red blood cell layer is about 90% and the inner annular plasma layer is substantially devoid of cells. In more details, at the outcome of this sedimentation stage, the separation bag 1 exhibits four layers: a first inner layer mainly comprising plasma, a second intermediate layer mainly comprising platelets, a third intermediate layer mainly comprising white blood cells (lymphocytes, monocytes and granulocytes), and a fourth outer layer mainly comprising red blood cells, wherein the third and fourth layers partially overlap (the granulocytes are in part embedded in the fourth layer).

Fifth stage (first protocol): a plasma component is transferred into the third satellite bag 4.

At the onset of this stage, the three pinch valve members 42, 43, 44 are closed. The rotor is rotated at the same high centrifugation speed as in the sedimentation stage. After a predetermined period of time after the intermediate sensor 72 has detected the outwards moving plasma/blood cell interface, which can happen before the end of the predetermined sedimentation period, the third pinch valve member 44 controlling access to the third satellite bag 4 is opened and the pumping station 60 is actuated so as to pump hydraulic liquid at a constant flow rate (for example, about 220 ml/min) into the hydraulic chamber 56. The expanding hydraulic chamber 56 squeezes the separation bag 1 and causes the transfer of plasma into the third satellite bag 4. The pumping station 60 is stopped and the third pinch valve member 44 is closed after a predetermined period of time has elapsed following the detection of the plasma/blood cell interface by the inner sensor 70. At the end of this stage, a first, major, fraction of the total volume of plasma is in the third satellite bag 4, whereas a second, residual, fraction of the total volume of plasma remains in the separation bag 1.

The transfer flow rate of the plasma component (which is directly related to the flow rate of the hydraulic fluid) is selected to be as high as possible without disturbing the platelet layer so as to avoid contaminating the plasma component with platelets.

Sixth stage (first protocol): a platelet/mononuclear cell component is transferred into the first satellite bag 2.

The sixth stage can start as soon as the third pinch valve member 44 is closed at the end of the fifth stage. At the onset of this fifth stage, the pinch valve members 42, 43, 44 are closed. The rotor is rotated at the same high centrifugation speed as previously. The first pinch valve member 42 controlling access to the first satellite bag 2 is opened and the pumping station 60 is actuated so as to pump hydraulic liquid at a constant flow rate (for example, about 140 ml/min) into the hydraulic chamber 56. The expanding hydraulic chamber 56 squeezes the separation bag 1 and causes the transfer, into the first satellite bag 2, of a platelet/mononuclear cell component comprising the residual volume of plasma, the platelets, lymphocytes, monocytes and a small amount of red blood cells. The pumping station 60 is stopped and the first pinch valve member 42 is closed after a predetermined volume has been transferred into the first satellite bag 2, which corresponds to a determined volume of hydraulic liquid pumped into the hydraulic chamber 56 (which in turn can be determined by a number of steps of the step motor 63).

For example, the predetermined volume of the platelet/mononuclear cell component can be set at about between 10 and 15 ml, including about 5 ml of plasma and about 5 ml of red bloods cells.

Seventh stage (first protocol): a volume of wash solution is transferred from the second satellite bag 3 into the separation bag 1.

At the onset of this stage, the pinch valve members 42, 43, 44 are closed. The speed of the centrifuge is decreased to a third centrifugation speed (for example, about 1000 RPM) at which the pumping station 60 can pump hydraulic liquid out of the hydraulic chamber 56. The pumping station 60 is actuated so as to pump from the hydraulic chamber 56 a volume of hydraulic liquid corresponding to the volume of wash solution in the second satellite bag 3. The pumping station 60 is controlled so as to pump hydraulic liquid at a fast flow rate (for example 500 ml/min).

The second pinch valve member 43 is opened for a predetermined amount of time so as to allow the transfer into the separation bag 1, under centrifugation forces, of the total volume of wash solution contained in the second satellite bag 3.

Eighth stage (first protocol): the red blood cells are mixed with the wash solution.

At the onset of this stage, the three pinch valve members 42, 43, 44 are closed.

In one embodiment, the rotation speed of the rotor is decreased until the rotor stops. The motor 40 is controlled so as to rotate the rotor back and forth of a determined angle (for example, 180°) in each direction for a predetermined amount of time for mixing.

In another variation, the rotation speed of the rotor is cyclically sharply increased and decreased from the third rotation speed to a fourth rotation speed (for example, 2500 RPM) for a determined period of time.

Ninth stage (first protocol): the mixture of red blood cells and wash solution is sedimented to desired layers.

At the onset of this stage, the three pinch valve members 42, 43, 44 are closed. The speed of the rotor is increased steadily until it reaches the second, high, centrifugation speed (for example, about 3200 RPM) at which the red blood cells are separated from a supernatant (used wash solution containing plasma and, possibly, undesirable proteins and viruses). In more detail, the rotor is rotated at the second centrifugation speed for a predetermined period of time (for example, about 220 seconds), which is selected so that, whatever the concentration of red blood cells in the mixture, the red blood cells sediment therein at the end of the predetermined period to a point where the hematocrit in the outer annular red blood cell layer is about 90% and the inner annular supernatant layer is substantially devoid of cells.

Tenth stage (first protocol): a supernatant component is transferred into the second satellite bag 3 (which initially contained wash solution).

At the onset of this stage, the three pinch valve members 42, 43, 44 are closed. The rotor is rotated at the same high centrifugation speed as in the sedimentation stage. After a predetermined period of time after the intermediate sensor 72 has detected the outwards moving supernatant/blood cell interface, which can happen before the end of the predetermined sedimentation period, the second pinch valve member 43 controlling access to the second satellite bag 3 is opened and the pumping station 60 is actuated so as to pump hydraulic liquid at a constant flow rate (for example, about 220 ml/min) into the hydraulic chamber 56. The expanding hydraulic chamber 56 squeezes the separation bag 1 and causes the transfer of a supernatant component into the second satellite bag 3 used as a waste bag. The pumping station 60 is stopped and the second pinch valve member 43 is closed after a predetermined period of time has elapsed following the detection of the supernatant/blood cell interface by the inner sensor 70. At the end of this stage, the separation bag essentially contains washed red blood cells.

Eleventh stage (first protocol): the centrifugation process is ended.

The rotation speed of the rotor is decreased until the rotor stops, the pumping system 60 is actuated so as to pump the hydraulic liquid from the hydraulic chamber 56 at a high flow rate (for example, about 800 ml/min) until the hydraulic chamber 56 is substantially empty, and the pinch valve members 42, 43, 44 are actuated so as to seal and cut the transfer tubes 20, 25, 26. Washed red blood cells remain in the separation bag 1.

Twelfth stage (first protocol): a red blood cell component is transferred into the fourth satellite bag 5.

The lid 50 of the rotor is opened and the separation bag 1 connected to the fourth satellite bag 5 is removed therefrom. The clamp 24 on the transfer tube 27 is opened. The frangible connector 21 blocking communication between the fourth satellite bag 5 and the leuko-reduction filter 28 is broken. The storage solution contained in the fourth satellite bag 5 is allowed to flow by gravity through the filter 28 and into the separation bag 1 where it is mixed with the red blood cells so as to lower the viscosity thereof. The content of the separation bag 1 is then allowed to flow by gravity through the filter 28 and into the fourth satellite bag 5. The white blood cells (granulocytes and residual monocytes and lymphocytes) are trapped by the filter 28, so that the ultimate packed red blood cell component in the fourth satellite bag 5, in addition to be substantially depleted from undesirable proteins and viruses, is substantially devoid from white blood cells and meets the standard of the AABB (American Association of Blood Banks), which is less than $5 \times 10^6$ white blood cells per packed red blood cell component.

An example of a second separation protocol aiming at the preparation of two blood components from a whole blood donation, namely a plasma component and (twice washed) red blood cell component, is explained below.

The second protocol differs from the first protocol essentially in that:

Red blood cells are washed twice instead of once;

The supernatant component, after each separation stage, is transferred into the first satellite bag 2, which is used as a waste bag; and The platelet/mononuclear cell component, instead of being isolated for further processing, is discarded with the supernatant component.

The operation of the separation apparatus along the second separation protocol is as follows:

Stages 1 to 6 (second protocol) are identical to stages 1 to 6 of the first protocol.

Seventh stage (second protocol): a determined volume of wash solution is transferred from the second satellite bag 3 into the separation bag 1.

At the onset of this stage, the pinch valve members 42, 43, 44 are closed. The speed of the centrifuge is decreased to a third centrifugation speed (for example, about 1000 RPM) at which the pumping station 60 can pump hydraulic liquid out of the hydraulic chamber 56. The pumping station 60 is actuated so as to pump from the hydraulic chamber 56 a volume of hydraulic liquid corresponding to half of the total volume of wash solution in the second satellite bag 3. The pumping station 60 is controlled so as to pump hydraulic liquid at a fast flow rate (for example 500 ml/min).

The second pinch valve member 43 is opened for a predetermined amount of time so as to allow the transfer into the separation bag 1, under centrifugation forces, of half of the total volume of wash solution contained in the second satellite bag 3.

Eighth stage (second protocol): the red blood cells are mixed with the wash solution.

This stage essentially corresponds to the eighth stage of the first protocol.

Ninth stage (second protocol): the mixture of red blood cells and wash solution is sedimented to desired layers.

This stage essentially corresponds to the ninth stage of the first protocol.

Tenth stage (second protocol): a supernatant component is transferred into the first satellite bag 2, in which the platelet/mononuclear cell component has previously been transferred. According to this second protocol, the first satellite bag 2 is therefore used as a waste bag.

At the onset of this stage, the three pinch valve members 42, 43, 44 are closed. The rotor is rotated at the same high centrifugation speed as in the sedimentation stage. After a predetermined period of time after the intermediate sensor 72 has detected the outwards moving supernatant/blood cell interface, which can happen before the end of the predetermined sedimentation period, the first pinch valve member 42 controlling access to the first satellite bag 2 is opened and the pumping station 60 is actuated so as to pump hydraulic liquid at a constant flow rate (for example, about 220 ml/min) into the hydraulic chamber 56. The expanding hydraulic chamber 56 squeezes the separation bag 1 and causes the transfer of a supernatant component into the first satellite bag 2 used as a waste bag. The pumping station 60 is stopped and the first pinch valve member 43 is closed after a predetermined period of time has elapsed following the detection of the supernatant/blood cell interface by the inner sensor 70. At the end of this stage, the separation bag essentially contains once washed red blood cells.

Stages 7 to 10 are repeated once, so that the second half of the volume of wash solution remaining in the satellite bag 3 is transferred into the separation bag 1, it is mixed with the once washed red blood cells, the mixture is centrifuged so as to separate twice washed red blood cells and a supernatant component, and the supernatant component is transferred into the first satellite bag 2, which already contains the platelet/mononuclear cell component and the first half of the used was solution.

The last two stages of the second protocol are identical to the eleventh and twelfth stages of the first protocol.

In a variation of the second protocol, the red blood cells instead of being washed twice are washed three times or more, for example each time with the same amount of wash solution.

A third separation protocol consists in preparing two blood components from a volume of whole blood, namely a platelet rich plasma component and a washed red blood cell component.

In accordance with the third protocol:

A volume of whole blood contained in a separation bag 1 is subjected to a "soft spin" centrifugation process (for example, about 2000 RPM), at the end of which the separation bag 1 exhibits three layers: a first inner layer mainly comprising plasma in which most of the platelets are suspended (platelet rich plasma), an intermediate layer mainly comprising white blood cells (lymphocytes, monocytes and granulocytes), and a third outer layer mainly comprising red blood cells, wherein the third and fourth layers partially overlap (the granulocytes are in part embedded in the fourth layer).

A platelet rich plasma component is transferred into the third satellite bag 4, while the rotation speed of the rotor remains the same.

The separation bag 1 is then subjected to a "hard spin" centrifugation (for example, about 3200 RPM) for a predetermined amount of time, so as to extract remaining plasma from highly packed red blood cells (for example, about 90 hematocrit).

A mononuclear cell component comprising plasma, mononuclear cells and a few red blood cells is then transferred into the first satellite bag 2, which is used as a waste bag.

The packed red cells remaining in the separation bag 1 are then washed with the wash solution contained in the second satellite bag 3, either once with the whole content of the second satellite bag 3, or two or more times, each time with a fraction of the content of the second satellite bag 3, and the supernatant, either all at once or in several installment, is transferred into the first satellite bag 2.

In another embodiment of the third protocol the mononuclear cell component is not discarded but rather after the platelet rich plasma has been transferred into the third satellite bag 4, the red blood cells are washed as many times as desired. All the white cells are removed by filtration from the final red blood cell product.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. A method for separating a volume of whole blood into at least a plasma component and a red blood cell component comprising:
   loading a disposable set comprising a separation bag and at least a wash solution bag onto the rotor of a centrifuge;
   centrifuging the separation bag containing a volume of whole blood so as to separate therein at least a first component comprising plasma and a second component comprising red blood cells and an intermediate component comprising platelets and mononuclear cells;
   transferring, on the rotor, the first component into a plasma component bag connected to the separation bag, during centrifugation of the separation bag;
   transferring, on the rotor, the intermediate component into an intermediate component bag connected to the separation bag during centrifugation of the separation bag;
   transferring by centrifugation, on the rotor, into the separation bag a volume of wash solution from the wash solution bag on the rotor during centrifugation of the separation bag;
   mixing the volume of wash solution with the second component;
   centrifuging the separation bag so as to separate therein a washed red blood cell component and a supernatant component comprising used wash solution; and
   transferring, on the rotor, the supernatant component into a waste bag connected to the separation bag, during centrifugation of the separation bag.

2. Method according to claim 1, further comprising transferring the volume of whole blood into the separation bag from a whole blood bag connected to the separation bag.

3. Method according to claim 2, wherein the whole blood bag is on the rotor and the volume of whole blood is transferred by centrifugation from the whole blood bag into the separation bag.

4. Method according to claim 1, further comprising:
   transferring the volume of whole blood into the separation bag from a whole blood bag connected to the separation bag; and
   transferring the intermediate component into the whole blood bag, after the volume of whole blood has been transferred into the separation bag.

5. Method according to claim 1, wherein the volume of wash solution that is transferred into the separation bag substantially corresponds to a total volume of wash solution initially contained in the wash solution bag.

6. Method according to claim 5, wherein the supernatant component is transferred into the wash solution bag, which is used as the waste bag after the wash solution has been transferred into the separation bag.

7. Method according to claim 1, wherein the volume of wash solution that is transferred into the separation bag is a first fraction of a total volume of wash solution initially contained in the wash solution bag.

8. Method according to claim 7, further comprising:
   transferring the volume of whole blood into the separation bag from a whole blood bag connected to the separation bag; and
   transferring the supernatant component from the separation bag into the whole blood bag, which is used as the waste bag after the volume of whole blood has been transferred into the separation bag.

9. Method according to claim 7, further comprising, after transferring the supernatant component into a waste bag:
   transferring into the separation bag a second fraction of the total volume of wash solution initially contained in the wash solution bag, during centrifugation of the separation bag;
   mixing the wash solution with the second component;
   centrifuging the separation bag so as to separate therein a washed red blood cell component and a supernatant component comprising used wash solution; and
   transferring the supernatant component into the waste bag during centrifugation of the separation bag.

10. Method according to claim 1, wherein mixing the volume of wash solution with the second component comprises varying a centrifugation speed.

11. Method according to claim 1, wherein mixing the volume of wash solution with the second component comprises subjecting the separation bag to a back and forth move around a rotation axis.

12. Method according to claim 1, further comprising initially enclosing the separation bag in a separation compartment having a fixed internal volume.

13. Method according to claim 12, wherein transferring the first component into a plasma component bag comprises:
   allowing a fluid communication between the separation bag and the plasma component bag;
   pumping a fluid into the separation compartment so as to squeeze the separation bag until the first component has substantially been transferred into the plasma component bag.

14. Method according to claim 13, wherein transferring a volume of wash solution into the separation bag comprises:
   pumping a volume of fluid from the separation compartment after the first component has been transferred into the plasma component bag;

allowing fluid communication between the separation bag and the wash solution bag so as to transfer a volume of wash solution into the separation bag.

15. Method according to claim 14, wherein the volume of fluid that is pumped out of the separation compartment substantially corresponds to a determined volume of wash solution to be transferred into the separation bag.

16. Method according to claim 1, further comprising transferring a volume of storage solution for red blood cells into the separation bag, after transferring the supernatant component into the waste bag.

17. Method according to claim 16, wherein the volume of storage solution is initially contained in a red blood cell product bag connected to the separation bag and the volume of storage solution is transferred from the red blood cell product bag into the separation bag.

18. Method according to claim 17, further comprising mixing the volume of storage solution with the second component.

19. Method according to claim 18, further comprising transferring the mixture of storage solution and second component into the red blood cell product bag.

20. Method according to claim 19, further comprising filtering the mixture of storage solution and second component through a leuko-depletion filter while the mixture is being transferred into the red blood cell product bag.

* * * * *